United States Patent [19]

Adams et al.

[11] Patent Number: 5,652,255

[45] Date of Patent: Jul. 29, 1997

[54] POTENTIATION OF BIOREDUCTIVE AGENTS

[75] Inventors: Gerald Edward Adams; Ian James Stratford; Pauline Joy Wood, all of Didcot, United Kingdom

[73] Assignee: British Technology Group Limited, London, England

[21] Appl. No.: 235,315

[22] Filed: Apr. 29, 1994

[30] Foreign Application Priority Data

Mar. 7, 1994 [GB] United Kingdom .................. 9404400

[51] Int. Cl.$^6$ .................... A61K 31/415; A61K 31/22; A61K 31/195
[52] U.S. Cl. .................... 514/398; 514/403; 514/551; 514/564; 514/565
[58] Field of Search .................... 514/398, 565, 514/564, 403, 515

[56] References Cited

U.S. PATENT DOCUMENTS

| 4,954,515 | 9/1990 | Suto ........................................ 514/398 |
| 5,098,921 | 3/1992 | Adams et al. ........................... 514/383 |

FOREIGN PATENT DOCUMENTS

| 0 446 699 A1 | 9/1991 | European Pat. Off. . |
| 2 240 041 | 7/1991 | United Kingdom . |
| WO 93/13055 | 7/1993 | WIPO . |

OTHER PUBLICATIONS

P.J. Wood et al. "Modification of energy metabolism and radiation . . . " Biochemical & Biophysical Communications, vol. 192 No. 2, Apr. 29 1993, pp. 505–510.

G.E. Adams. "Redox, radiation, and reductive bioactivation" Radiation Research, 132 (1992), pp. 129–139.

P.K. Moore et al. "Characterization of the novel nitric oxide . . . " Br. J. Pharmacol. (1993) 110, pp. 219–224.

Khalid Hasan et al. "Inhibition of nitric oxide formation by guanidines" European Journal of Pharmacology, 249 (1993), pp. 101–106.

S. Moncada et al. "Mechanism of action of some inhibitors . . . " Proc. Natl. Acad. Sci. USA, vol. 83, Dec. 1986, pp. 9164–9168.

C. Thiemermann et al. "Inhibition of the release of endothelium–derived . . . " Br. J. Pharmacol. (1991), 104, pp. 31–38.

R.C. Babbedge et al. "L–N$^G$–nitro arginine P–nitroanilide . . . " British Journal of Pharmacology, 1992, 107 p. 194.

S. Moncada et al. "Nitric Oxide: Physiology, pathophysiology . . . " Pharmacological Reviews, vol. 49 No. 2, pp. 109–142. 1991.

C. Thiemermann. "Biosynthesis and interaction of endothelium–derived . . . " Eicosanoids, Springer–Verlage, 1991, pp. 187–202.

C. Szabo et al. "Dihydropyridine calcium channel modulators . . . " Biochem. Biophys. Res. Commun. 196, (1983), pp. 825–830.

G.E. Adams. "Bioreductive drugs for cancer therapy: the search . . . " Intl Journal of Radiation Oncology, vol. 29 No. 2, May 15, 1994, pp. 231–238.

Pauline J. Wood et al, "Induction of Hypoxia in Experimental Murine Tumours . . . ", Cancer Research, 54, 6458–6463, Dec. 15, 1994.

Terence C. Jenkins et al, "Synthesis and Evaluation of . . . ", Journal of Medicinal Chemistry, 1990, 33, 2603–2610.

I. Ahmed et al, "Analogues of RSU–1069: Radiosensitisation and Toxicity In vitro and In vivo", Int. J. Radiation Oncology Biol. Phys. vol. 12, 1079–1081, 1986.

Robert A. Gatenby et al, "Oxygen Distribution in Squamous Cell Carcinoma Metastases . . . ", Int. J. Radiation Oncology Biol. Phys. vol. 14, 831–838, 1988.

M. Höckel et al, "Oxygenation of Carcinomas of the Uterine Cervix . . . ", Cancer Research 51, 6098–6102, Nov. 15, 1991.

P. Vaupel et al, "Oxygenation of Human Tumours: Evaluation of Tissue Oxygen Distribution . . . ", Cancer Research 51, 3316–3322, Jun. 15, 1991.

E. Lartigau et al, "Mésure de la pression partielle en oxygéne . . . ", Bull Cancer/Radiother (1992), 79, 199–206.

Sara Rockwell and John E. Moulder, "Hypoxic Fractions of Human Tumours xenografted into mice: a Review", Int. J. Radiation Oncology Biol. Phys. vol. 19, pp. 197–202, 1990.

*Primary Examiner*—Jerome D. Goldberg
*Attorney, Agent, or Firm*—Nixon & Vanderhye

[57] ABSTRACT

A human or animal subject having a solid tumour is treated by administering to the subject therapeutically effective amounts of a nitric oxide (NO) synthase inhibitor and a compound which is an imidazole or 1,2,4-triazole derivative of formula (A)

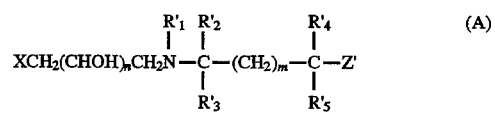

wherein X is selected from the group consisting of

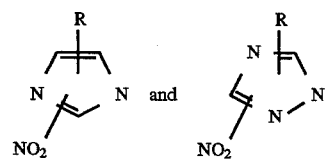

wherein R is hydrogen or a $C_1$–$C_6$ alkyl group; each of $R'_1$ to $R'_5$ is independently selected from the group consisting of hydrogen, $C_1$–$C_6$ alkyl, hydroxy($C_1$–$C_6$ alkyl), phenyl, ($C_1$–$C_6$ alkyl)phenyl and phenyl($C_1$–$C_6$ alkyl); m is 0 or 1; n is 1 or 2; and Z' represents a leaving group which has the potential for expulsion via an intramolecular cyclisation reaction and which is not negatively-charged; or a physiologically acceptable acid addition salt thereof.

17 Claims, 3 Drawing Sheets

POTENTIATION OF BIOREDUCTIVE AGENTS

FIELD OF THE INVENTION

The invention relates to a method of treating a human or animal subject having a solid tumour with a bioreductive drug.

BACKGROUND TO THE INVENTION

EP-A-0 319 329 discloses that compounds of the following formula (A') and salts thereof are useful as bioreductive drugs for treating tumours:

$$XCH_2(CHOH)_nCH_2N-\underset{\underset{R_3'}{|}}{\overset{\overset{R_1'}{|}}{C}}-\underset{\underset{R_3'}{|}}{\overset{\overset{R_2'}{|}}{}}(CH_2)_m-\underset{\underset{R_5'}{|}}{\overset{\overset{R_4'}{|}}{C}}-Z' \quad (A')$$

wherein X represents a nitro-substituted aromatic or heteroaromatic group with a one-electron reduction potential at pH 7 of from −250 to −500 mV; each of $R'_1$ to $R'_5$ independently represents hydrogen or an alkyl, hydroxyalkyl, aryl, aralkyl or alkaryl group; m is 0 or 1; n is 1 or 2; and Z' represents a leaving group which has the potential for expulsion via an intramolecular cyclisation reaction.

A preferred bioreductive compound disclosed in EP-A-0 319 329 for treating tumours is 1-(2-nitro-1-imidazolyl)-3-(2-bromoethylamino)-2-propanol hydrobromide (RB6145).

Nitric oxide (NO) synthase inhibitors have been proposed as useful for treating a variety of diseases. NO synthase produces NO from L-arginine. Local release of NO from the vascular endothelium causes dilation of blood vessels; for review see Moncada et al (1991) Pharmacol. Rev. 43, 109–141. The inhibition of NO synthase by compounds such as L-arginine analogues causes constriction of blood vessels, which results in a localised reduction of blood perfusion and/or increased blood pressure (Thiemermann (1991) Eicosanoids 4, 187–202).

We have recently studied the effects of enhancing or reducing NO availability in solid tumours (Wood et al (April 1993) Biochemical and Biophysical Research Communications 192, 505–510). We discovered that the NO synthase inhibitor nitro-L-arginine causes a sustained reduction in the amount of oxygen in the tumour. In contrast, we discovered that the NO donor SIN-1 increases tumour oxygenation.

SUMMARY OF THE INVENTION

We have now found that the therapeutic effect of the bioreductive drugs disclosed in EP-A-0 319 329 is greatly potentiated by NO synthase inhibitors. In contrast, the therapeutic effect of other bioreductive and chemotherapeutic drugs such as SR4233 (3-amino-1,2,4-benzotriazine-1,4-dioxide; Tirapazamine, Trade Name) and cyclophosphamide is enhanced little or not at all by NO synthase inhibitors.

Accordingly, the invention provides a method of treating a human or animal subject having a solid tumour, which method comprises administering to the subject therapeutically effective amounts of a nitric oxide (NO) synthase inhibitor and a compound which is an imidazole or 1,2,4-triazole derivative of formula (A)

$$XCH_2(CHOH)_nCH_2N-\underset{\underset{R'_3}{|}}{\overset{\overset{R'_1}{|}}{C}}-\underset{\underset{R'_3}{|}}{\overset{\overset{R'_2}{|}}{}}(CH_2)_m-\underset{\underset{R'_5}{|}}{\overset{\overset{R'_4}{|}}{C}}-Z' \quad (A)$$

wherein X is selected from the group consisting of

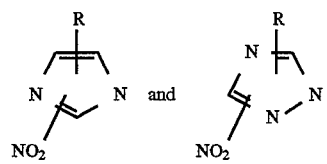

wherein R is hydrogen or a $C_1$–$C_6$ alkyl group; each of $R'_1$ to $R'_5$ is independently selected from the group consisting of hydrogen, $C_1$–$C_6$ alkyl, hydroxy($C_1$–$C_6$ alkyl), phenyl, ($C_1$–$C_6$ alkyl)phenyl and phenyl($C_1$–$C_6$ alkyl); m is 0 or 1; n is 1 or 2; and Z' represents a leaving group which has the potential for expulsion via an intramolecular cyclisation reaction and which is not negatively-charged; or a physiologically acceptable acid addition salt thereof.

DETAILED DESCRIPTION OF THE INVENTION

The Imidazole or 1,2,4-Triazole Derivative

X is one of the groups

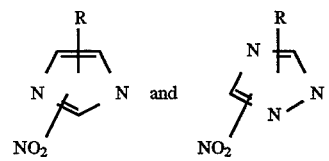

Figure 1A:
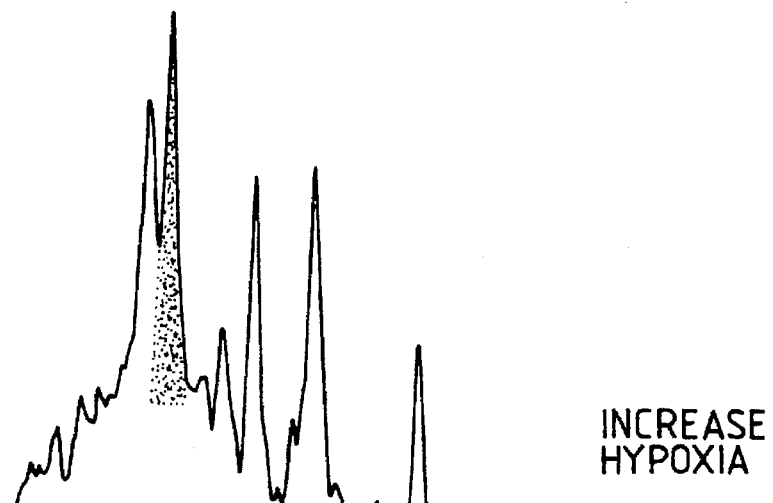
FIGS. 1A, 1B and 1C: These figures have been included to illustrate the changes that occur in the $^{31}$P MR spectrum of a typical murine transplantable tumour after either increasing hypoxia (increase in Pi/total) or increasing oxygenation (reduction in Pi/total).
Figure 1B:
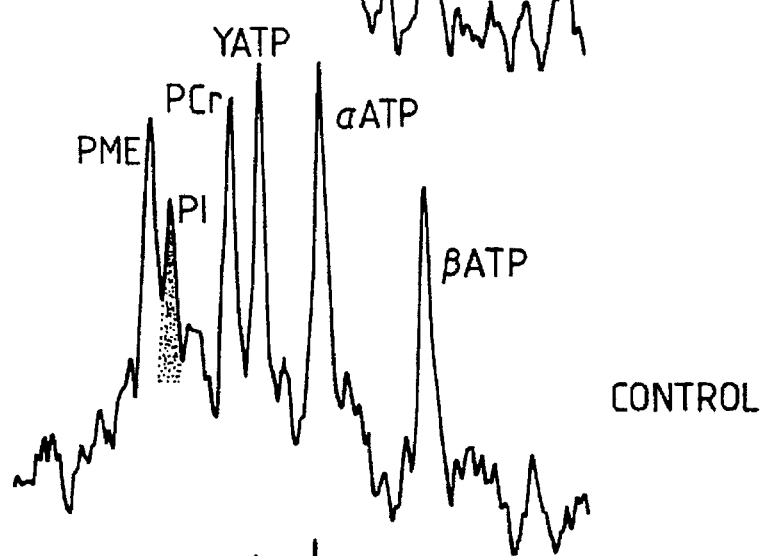
Figure 1C:
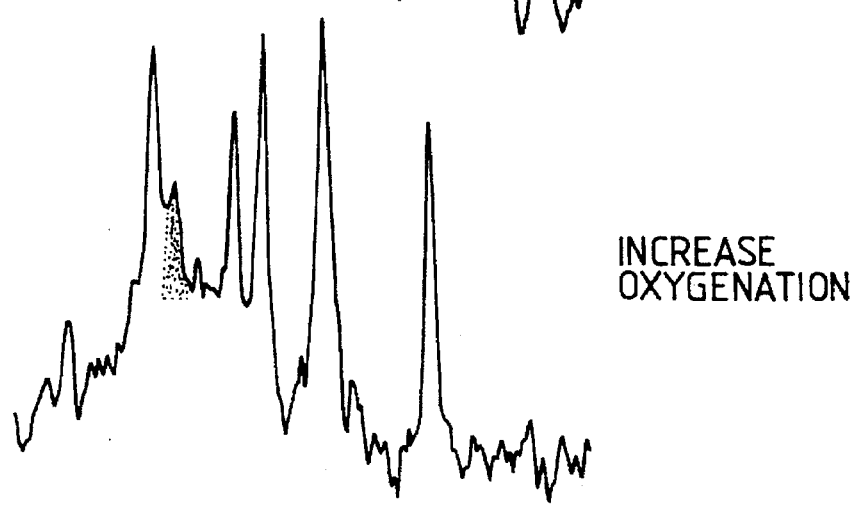

wherein R is hydrogen or a $C_1$–$C_6$ alkyl group. Preferably, R is hydrogen or methyl, most preferably hydrogen. R may be in the 2-, 4- or 5-position when X is imidazol-1-yl, and in the 3- or 5- position when X is 1,2,4-triazol-1-yl. The nitro group is preferably in the 2-position when X represents an imidazol-1-yl group or in the 3-position when X represents a 1,2,4-triazol-1-yl group.

Preferably, X is an imidazol-1-yl group, most preferably an imidazol-1-yl group with a nitro group at the 2-position.

The preferred value for m is 0 and for n is 1.

$R'_1$ to $R'_5$ are each independently hydrogen, $C_1$–$C_6$ alkyl, hydroxy($C_1$–$C_6$ alkyl), phenyl, ($C_1$–$C_6$ alkyl)phenyl or phenyl($C_1$–$C_6$ alkyl). A $C_1$–$C_6$ alkyl group is preferably methyl. A hydroxy($C_1$–$C_6$ alkyl) group may be hydroxymethyl, a phenyl($C_1$–$C_6$ alkyl) group may be benzyl, and a ($C_1$–$C_6$ alkyl)phenyl group may be methyl-substituted phenyl. Preferred compounds are compounds in which $R'_1$ is hydrogen and each of $R'_2$ to $R'_5$ is independently hydrogen or methyl. Examples of such compounds are those in which $R'_1$ is hydrogen and (a) $R'_2$ to $R'_5$ are each hydrogen or (b) $R'_2$ and $R'_3$ are hydrogen and $R'_4$ and $R'_5$ are methyl or (c) $R'_2$ and $R'_4$ are methyl and $R'_3$ and $R'_5$ are hydrogen or (d) $R'_2$ and $R'_3$ are methyl and $R'_4$ and $R'_5$ are hydrogen or (e) $R'_2$ to $R'_5$ are each methyl.

Z' is not a negatively charged group such as phosphate. Z' is, for example, selected from halogen;

—$OCOR_6$, —$OSOR_6$, —$OSO_2R_6$, —$OPO_5(R_6)_2$ and —$OP(O)(N(R_6)_2)_2$ wherein $R_6$ is selected from the group consisting of hydrogen; $C_1$–$C_6$ alkyl; halo($C_1$–$C_6$ alkyl); phenyl; phenyl($C_1$–$C_6$ alkyl); ($C_1$–$C_6$ alkyl)thio; amino; phenyl substituted with a substituent selected from the group consisting of $C_1$–$C_6$ alkyl, $C_1$–$C_6$ alkoxy, hydroxy, halogen, nitro, amino and trifluoromethyl; and, when Z' is —$OSO_2R_6$, hydroxy;

phenyloxy;

—$ONO_2$;

—$NHSO_2R_7$, —$NHCOR_7$, -$NHCO_3R_7$, and —$N(COR_7)_2$ wherein $R_7$ is selected from the group consisting of hydrogen, $C_1$–$C_6$ alkyl, phenyl and phenyl($C_1$–$C_6$ alkyl);

cyclic imide (such as succinimide and phthalimide); and —$N^+R^aR^bR^c$ and —$N(O)R^aR^b$ wherein $R^a$ is selected from the group consisting of $C_1$–$C_6$ alkyl, pyridine and imidazole and $R^b$ and $R^c$ are independently selected from $C_1$–$C_6$ alkyl groups.

From amongst these, Z' typically may be halogen or —$OCOR_6$ wherein $R_6$ is $C_1$–$C_6$ alkyl or halo($C_1$–$C_6$ alkyl). Preferred are halogen, $C_2$–$C_6$ alkanoyloxy and per- or poly-fluoro-$C_2$–$C_6$ alkanoyloxy. More preferred are fluorine, chlorine, bromine, iodine, acetoxy and trifluoroacetoxy. Most preferred is bromine.

Acid addition salts of the compounds of formula (A) may be salts with any physiologically acceptable acid. Examples of suitable acids are inorganic acids such as hydrochloric, hydrobromic and hydriodic acid. Organic acids may be used. Preferred are hydrohalic acids in which the halogen anion corresponds to the halogen denoted by the group Z', although this is not essential.

Certain classes of the imidazole and 1,2,4-triazole derivatives were not known prior to EP-A-0 319 329. These compounds include compounds of formula (B)

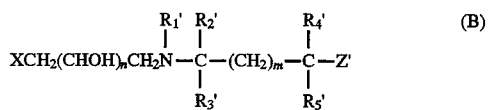
(B)

wherein X, $R'_1$ to $R'_5$, m, n and Z' are as defined above with the proviso that m is 1 when X represents

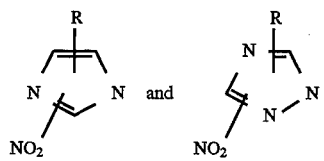

and R is hydrogen or a $C_1$–$C_6$ alkyl group, $R'_1$ is hydrogen, each of $R'_2$ to $R'_5$ is independently selected from the group consisting of hydrogen, $C_1$–$C_6$ alkyl, phenyl, ($C_1$–$C_6$ alkyl) phenyl and phenyl($C_1$–$C_6$ alkyl) and Z' represents halogen; and physiologically acceptable acid addition salts thereof.

Whilst the compounds of formula (B) and their salts can be used in the present invention, the preferred compounds for use in the invention generally fall within the proviso of formula (B). These are the compounds of formula (C)

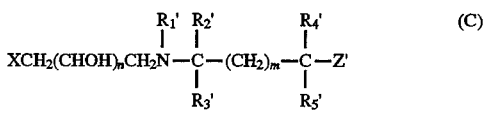
(C)

wherein m is 0, n is 1 or 2, X represents

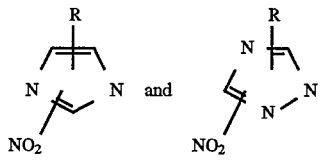

R is hydrogen or a $C_1$–$C_6$ alkyl group, $R'_1$ is hydrogen, each of $R'_2$ to $R'_5$ is independently selected from the group consisting of hydrogen, $C_1$–$C_6$ alkyl, phenyl, ($C_1$–$C_6$ alkyl) phenyl and phenyl($C_1$–$C_6$ alkyl) and Z' represents halogen; and physiologically acceptable acid addition salts thereof.

Particularly preferred compounds for use in the invention are 1-(2-nitro-1-imidazolyl)-3-(2-bromoethylamino)-2-propanol and its salts, especially the hydrobromide (RB6145). Examples of other compounds which may be used are 1-(2-nitro-1-imidazolyl)-3-(2-chloroethylamino)-2-propanol,
1-(2-nitro-1-imidazolyl)-3-(2-iodoethylamino)-2-propanol,
1-(2-nitro-1-imidazolyl)-3-(2-fluoroethylamino)-2-propanol,
1-(2-nitro-1-imidazolyl)-3-(2-acetoxyethylamino)-2-propanol,
1-(2-nitro-1-imidazolyl)-3-(2-trifluoroacetoxyethylamino)-2-propanol,
1-(2-methyl-4-nitro-1-imidazolyl)-3-(2-chloroethylamino)-2-propanol,
1-(2-methyl-4-nitro-1-imidazolyl)-3-(2-bromoethylamino)-2-propanol,
1-(2-methyl-4-nitro-1-imidazolyl)-3-(2-iodoethylamino-2-propanol,
1-(2-methyl-5-nitro-1-imidazolyl)-3-(2-chloroethylamino)-2-propanol,
1-(2-methyl-5-nitro-1-imidazolyl)-3-(2-bromoethylamino)-2-propanol,
1-(2-methyl-5-nitro-1-imidazolyl)-3-(2-iodoethylamino)-2-propanol,
1-(2-methyl-5-nitro-1-imidazolyl)-3-(2-fluoroethylamino)-2-propanol,
1-(3-nitro-1,2,4-triazol-1-yl)-3-(2-chloroethylamino)-2-propanol,
1-(3-nitro-1,2,4-triazole-1-yl)-3-(2-bromoethylamino)-2-propanol, 1-(2-nitro-1-imidazolyl)-3-(3-bromopropylamino)-2-propanol,
1-(2-nitro-1-imidazolyl)-3-(1-chloro-2-methyl-2-propylamino)-2-propanol,
1-(2-nitro-1-imidazolyl)-3-(1-bromo-2-methyl-2-propylamino)-2-propanol,
1-(2-nitro-1-imidazolyl)-3-(dl-threo-2-chloro-3-butylamino)-2-propanol,
1-(2-nitro-1-imidazolyl)-3-(dl-threo-2-bromo-3-butylamino)-2-propanol,
1-(2-nitro-1-imidazolyl)-3-(2-chloro-2,3-dimethyl-3-butylamino)-2-propanol,
1-(2-nitro-1-imidazolyl)-3-(2-bromo-2,3-dimethyl-3-butylamino)-2-propanol, and
physiologically acceptable acid addition salts thereof.

Examples of salts of the above compounds which may be used are 1-(2-nitro-1-imidazolyl)-3-(2-chloroethylamino)-2-propanol hydrochloride,
1-(2-nitro-1-imidazolyl)-3-(2-bromoethylamino)-2-propanol hydrobromide,
1-(2-nitro-1-imidazolyl)-3-(2-iodoethylamino)-2-propanol hydriodide,
1-(2-nitro-1-imidazolyl)-3-(2-fluoroethylamino)-2-propanol hydrochloride,
1-(2-nitro-1-imidazolyl)-3-(2-acetoxyethylamino)-2-propanol,
1-(2-nitro-1-imidazolyl)-3-(2-trifluoroacetoxyethylamino)-2-propanol,
1-(2-methyl-4-nitro-1-imidazolyl)-3-(2-chloroethylamino)-2-propanol hydrochloride,
1-(2-methyl-4-nitro-1-imidazolyl)-3-(2-bromoethylamino)-2-propanol hydrobromide,
1-(2-methyl-4-nitro-1-imidazolyl)-3-(2-iodoethylamino)-2-propanol hydriodide,
1-(2-methyl-5-nitro-1-imidazolyl)-3-(2-chloroethylamino)-2-propanol hydrochloride,
1-(2-methyl-5-nitro-1-imidazolyl)-3-(2-bromoethylamino)-2-propanol hydrobromide,
1-(2-methyl-5-nitro-1-imidazolyl)-3-(2-iodoethylamino)-2-propanol hydriodide,
1-(2-methyl-5-nitro-1-imidazolyl)-3-(2-fluoroethylamino)-2-propanol hydrochloride,
1-(3-nitro-1,2,4-triazol-1-yl)-3-(2-chloroethylamino)-2-propanol hydrochloride,
1-(3-nitro-1,2,4-triazol-1-yl)-3-(2-bromoethylamino)-2-propanol hydrobromide,
1-(2-nitro-1-imidazolyl)-3-(3-bromopropylamino)-2-propanol hydrobromide,
1-(2-nitro-1-imidazolyl)-3-(1-chloro-2-methyl-2-propylamino)-2-propanol hydrochloride,
1-(2-nitro-1-imidazolyl)-3-(1-bromo-2-methyl-2-propylamino)-2-propanol hydrobromide,
1-(2-nitro-1-imidazolyl)-3-(dl-threo-2-chloro-3-butylamino)-2-propanol hydrochloride,
1-(2-nitro-1-imidazolyl)-3-(dl-threo-2-bromo-3-butylamino)-2-propanol hydrobromide,
1-(2-nitro-1-imidazolyl)-3-(2-chloro-2,3-dimethyl-3-butylamino)-2-propanol hydrochloride, and
1-(2-nitro-1-imidazolyl)-3-(2-bromo-2,3-dimethyl-3-butylamino)-2-propanol hydrobromide.

The imidazole and 1,2,4-triazole derivatives for use in the invention may be synthesized as described in EP-A-0 319 329.

The imidazole and 1,2,4-triazole derivatives for use in the method of the invention exist in (R) and (S) enantiomeric forms which differ in the steric configuration of the $XCH_2$ $(C*HOH)_n$— moiety. The (R) enantiomers are particularly useful because they tend to be substantially devoid of emetic side effects (i.e. side effects which cause vomiting).

Preferred imidazole derivatives are the (R) enantiomers of the compounds of formula (A) and physiologically acceptable salts thereof wherein X is imidazol-1-yl having a nitro group at the 2-position; n is 1; m is 0; $R'_1$ to $R'_5$ are all hydrogen; and Z' is selected from the group consisting of halogen (e.g. chlorine or bromine), $—OSO_2R_6$ wherein $R_6$ is hydroxy, methyl, phenyl or phenyl substituted with a substituent selected from the group consisting of $C_1$–$C_6$ alkyl, $C_1$–$C_6$ alkoxy, hydroxy, halogen, nitro, amino and trifluoromethyl. Particularly preferred compounds are (R)-(+)-α-1-(2-nitro-1-imidazolyl)-3-(2-bromoethylamino)-2-propanol and its salts, especially the hydrobromide (RB6145).

The enantiomers may be prepared by a process which comprises reacting chiral 2-nitro-1-(2-oxiranylmethyl)-1H-imidazole with a 2-oxazolidinone of the formula

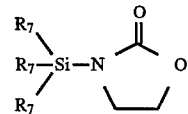

wherein $R_7$ is a $C_1$–$C_4$ alkyl group, phenyl or phenyl substituted with $C_1$–$C_4$ alkyl, $C_1$–$C_4$ alkoxy, hydroxy, halogen such as chlorine, bromine or fluorine, nitro, amino or trifluoromethyl, in the presence of a suitable catalyst to give a chiral compound of the formula

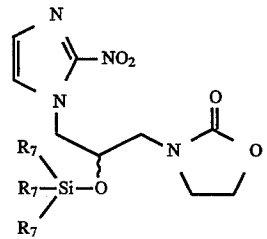

wherein $R_7$ is as defined above, which is:

(a) hydrolyzed, for example with potassium fluoride in methanol or acetic acid in methanol, to give chiral 3-[2-hydroxy-3-(2-nitro-1H-imidazol-1-yl)propyl]-2-oxazolidinone which is treated with an appropriate acid of formula HZ' wherein Z' is as defined above, preferably in acetic acid, the preferred acid being hydrobromic acid; or (b) treated in one step with such an acid.

Enantiomers of imidazole derivatives for use in the invention may thus be prepared as depicted in Chart I below.

CHART I
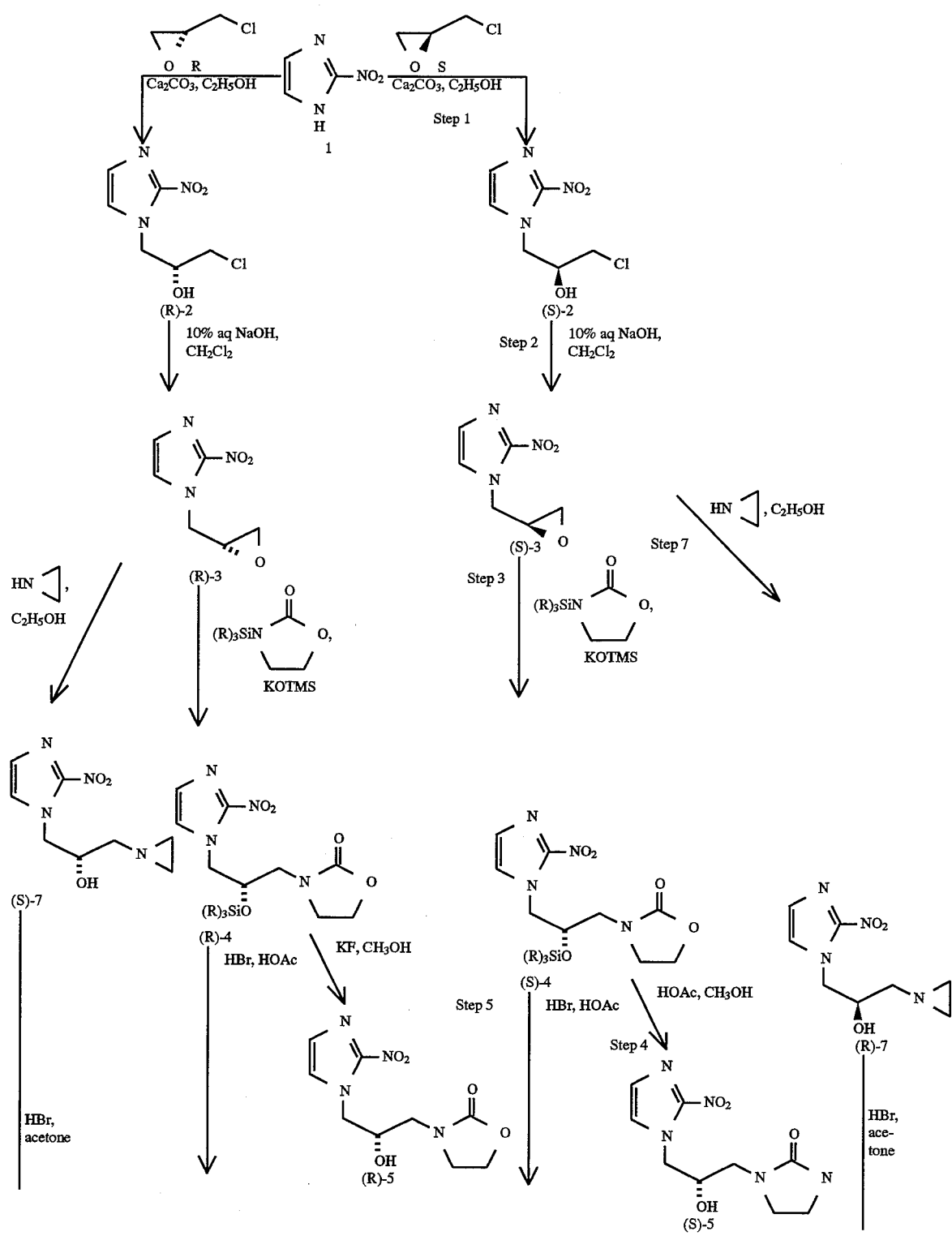

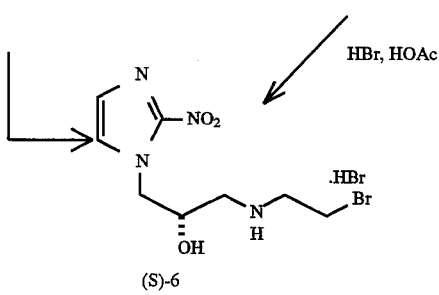

(S)-6

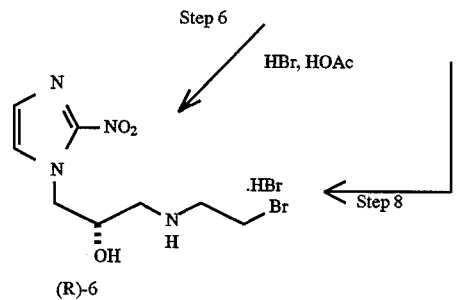

(R)-6

$(R)_3Si$=tri-R-silyl, preferably trimethylsilyl

Although the preferred reagents and solvents are depicted in each of the steps, it is readily apparent that the reaction conditions may be varied somewhat. For example, in Step 1, suitable solvents include epichlorohydrin alone, lower aliphatic alcohols, water, ethers such as diethyl ether, and diisopropyl ether or tetrahydrofuran, and lower dialkyl ketones such as acetone. Typical bases that can be used include essentially all metal carbonates, especially those of Group I metals (Na, K, Rb, Cs), also common amine bases such as the tertiary lower alkyl amines (triethylamine, diisopropyl ethylamine, N-Me-pyrrolidine, etc). Also common metal hydrides such as NaH. Quaternary ammonium bases such as $nBu_4N^+OH^-$, $nBu_4N^+Cl^-$, etc; various fluoride bases such as $nBu_4NF$, KF, CsF, etc. The temperature of the reaction in Step 1 can vary from room temperature to about 150° C.

In step 2 of Chart I typical solvents which can be employed include various ethers, lower alcohols; other chlorinated solvents, aromatic hydrocarbons such as benzene, toluene; dipolar aprotic solvents such as DMF, lower dialkyl ketones, lower alkyl nitriles. In step 2 the temperature can vary from −50° C. to 50° C. and the bases used can be the same as in step 1.

In step 3 of Chart I, in addition to using 3-tri-R-silyl-2-oxazolidinone neat as the solvent, other solvents which can be employed include various ethers, chlorinated hydrocarbons, dipolar aprotic solvents such as DMF, lower alkyl nitriles such as acetonitrile, aromatic hydrocarbons, and lower dialkyl ketones such as acetone. In addition to potassium silanolate, other catalysts which can be employed include other metal silanolates, metal alkoxides, various metal and quaternary ammonium fluorides such as KF, CsF, $nBu_4N^+F^-$, etc. The temperatures can vary from 0° C. to 250° C. and the preferred oxazolidinone is 3-trimethylsilyl-2-oxazolidinone.

In Step 4 of Chart I suitable solvents include water, lower alcohols, ethers, and lower alkyl organic acids such as acetic acid and the temperature can vary from 0° C. to 120° C. Suitable catalysts include mineral acids, strong organic acids such as trifluoroacetic acid, and those noted as suitable for Step 3.

In each of Steps 5 and 6 of Chart I, suitable solvents include lower alkyl organic acids and lower alkyl alcohols and acids can be mineral acids but preferably hydrobromic acid.

Chart I also depicts Steps 7 and 8 which represent an alternative method to prepare the chiral imidazole derivatives. The oxirane intermediate from Step 2 is reacted with aziridine in an alcoholic solvent. The resulting chiral aziridine intermediate is ring opened with mineral acid in an organic solvent, preferably by hydrobromic acid in acetone.

(R)-(+)-α-1-(2-Nitro-1-imidazolyl)-3-(2-bromoethylamino)-2-propanol monohydrobromide can be synthesized by the following steps (a) to (f).

(a) (S)-(+)-α-(Chloromethyl)-2-nitro-1H-imidazole-1-ethanol

A stirred suspension of 75.6 g (669 mmole) of 2-nitroimidazole, 10.9 g (33.5 mmole) of anhydrous caesium carbonate and 1.3 L of absolute ethanol maintained under nitrogen at room temperature is treated with 68 mL (869 mmole) of (S)-(+)-epichlorohydrin. The mixture is heated to gentle reflux for 2 hours. The hot solution is filtered through a preheated pad of ethanol-moistened Celite®, the pad is washed with a little ethanol, and the filtrate is diluted with 170 mL of hexane. The filtrate is cooled at 0°–5° C. for 1 day. The resultant crystals are collected by filtration, washed with 120 mL ethyl acetate-:diethyl ether (1:1), and dried to give 101.5 g of product, 92.6% pure by HPLC. A 9.87 g sample is recrystallized from 195 mL of ethyl acetate to give 7.45 g of pure product, mp 128°–129° C.; $[\alpha]_D^{25}$=+2.39° [c1, methanol].

Alternatively, a mixture of 2-nitroimidazole, anhydrous potassium carbonate, and (S)-(+)-epichlorohydrin is refluxed for 10 minutes then filtered while hot. The filtrate is concentrated and cooled to give a solid. Crystallization from ethanol and further processing gives the product.

(b) (S)-(−)-2-Nitro-1-(2-oxiranylmethyl)-1H-imidazole

To a vigorously stirring ice-cold suspension of 100.5 g (489 mmole) of (S)-(+)-α-(chloromethyl)-2-nitro-1H-imidazole-1-ethanol in 1 L of dichloromethane is added over 1 minute 1 L of 10% aqueous sodium hydroxide. The biphasic mixture is stirred for 7.5 hours at 0°–5° C., then diluted with 500 mL each of chloroform and water. The phases are separated and the aqueous phase is extracted three times with 200 mL portions of chloroform. The combined organic phases are dried over magnesium sulfate and concentrated to leave 71.1 g of a yellow oil that crystallizes upon prolonged storage at 0°–5° C. The crystals are dried at 0.05 mm/25° C./8 hours to give 69.1 g of product, mp 42°–43° C., 98.4% pure by HPLC.

A portion (1.14 g) of the product is dissolved in 20 mL of ethyl acetate and the solution is loaded onto a silica gel (230–400 mesh) column (4×13 cm). The column is eluted with 1:1 ethyl acetate:cyclohexane. Pure product fractions are combined and evaporated to a solid that is crystallized from 14 mL of 5:2 hexane:ethyl acetate. The solution is kept at −5° to 0° C. for 6 hours and the solids are collected by filteration, washed with 20 mL of diethyl ether, and dried at 0.025 mm/25° C. to give 681 mg of product as pale yellow crystals, mp 43°–44° C., 99% pure by HPLC; $[\alpha]_D^{25}$=−82.18° [C1, methanol].

Alternatively, reaction of 0.56 g of (S)-(+)-α-(chloromethyl)-2-nitro-1H-imidazole-1-ethanol with 3 mL of 10% aqueous sodium hydroxide at 25° C. for 30 minutes followed by further processing as above gives 0.3 g of the product.

(c) (S)-3-[3-(2-Nitro-1H-imidazol-1-yl)-2-[(trimethylsilyl) oxy]propyl]-2-oxazolidinone Under a brisk stream of dry nitrogen, a vigorously stirring mixture of 40.3 mL (256 mmole) of 3-trimethylsilyl-2-oxazolidinone and 274 mg (2.1 mmole) of potassium trimethylsilanolate is heated to 95° C. To the solution is added over 10 minutes a solution of 36.15 g (214 mmole) of (S)-(−)-2-nitro-1-(2-oxiranylmethyl)-1H-imidazole in 26 mL of dry tetrahydrofuran during which an opening in the flask allows evaporation of solvent. The addition funnel is rinsed with 5 mL of solvent, and the flask is kept open for an additional 15 minutes.

After heating at 95° C. for a total of 1.5 hours, 3.4 mL of additional 3-trimethylsilyl-2-oxazolidinone is added to the solution. The mixture is heated for an additional 1.5 hours then concentrated at 0.8 mm/50° C./16 hours to give an oil that is dissolved in 100 mL of 2:1 ethyl acetate:cyclohexane. The solution is loaded onto a column containing an 8×16 cm pad of silica gel (230–400 mesh). The column is eluted with ~5 L of 2:1 ethyl acetate:cyclohexane. Product fractions are combined and concentrated first at 20 mm, then at 0.8 mm to give 71.45 g of an oil that solidifies on standing. The solids are diluted with 200 mL of tert-butyl methyl ether, and the suspension is refluxed for 45 minutes, cooled, and filtered. The solids are washed sparingly with tert-butyl methyl ether and dried to leave 37.18 g of pure product as a light yellow solid, mp 98°–100° C.; $[\alpha]D^{25}$ =+15.4° [c1, methanol].

The tert-butyl methyl ether filtrate is concentrated to leave ~30 g of a viscous oil that is dissolved in 100 mL of 1:1 ethyl acetate:cyclohexane. The solution is loaded onto an 8×16 cm pad of silica gel as above and the column is eluted with 1:1 ethyl acetate:cyclohexane until pure product appears. The column is then eluted with ~3 L of 2:1 ethyl acetate:cyclohexane. Pure product fractions are combined and concentrated as above to leave 13 g of a sticky solid that is triturated in 1:1 diethyl ether:ethyl acetate to leave 5.67 g of a second crop, mp 95°–98° C., after drying.

(d) (S)-3-[2-Hydroxy-3-(nitro-1H-imidazol-1-yl)propyl]-2-oxazolidinone

A solution of 10.51 g (32 mmole) of (S)-3-[3-(2-nitro-1H-imidazol-1-yl)-2-[(trimethyl-silyl)oxy]propyl]-2-oxazolidinone and 32 mL of 1:1 methanol:glacial acetic acid is stirred at 25° C. for 16 hours during which a precipitate forms. The suspension is diluted with 30 mL of absolute ethanol, and the solids are collected by filtration, washed with ethanol and dried to give 6.49 g of a pure white solid, mp 134°–136° C., 98.5% optically pure by chiral HPLC; $[\alpha]D^{25}$=−5.97° [c1, methanol].

The filtrate is concentrated to near dryness and the solids are dissolved in methanol. The solution is decolorized with charcoal, then filtered through a pad of silica gel (230–400 mesh). The filtrate volume is reduced to 20 mL and the solution is refrigerated overnight. The solids are collected by filtration, then dissolved in ~10 mL of methanol. The solution is refrigerated for 3 hours and the solids are collected by filtration, washed with methanol, and dried to leave a second crop as a light yellow solid, mp 134°–136° C. The combined filtrates from the above two crystallizations are concentrated to a solid that is crystallized from methanol as above to give a third crop of product, mp 134°–136° C. The second and third crops are combined and dried to leave 1.18 g of product, 100% optically pure by chiral HPLC; $[\alpha]D^{25}$ −5.92 [c1, methanol].

(e) (R)-(−)-α-(1-Aziridinylmethyl)-2-nitro-1H-imidazole-1-ethanol

A solution of 0.3 g (1.8 mmole) of (S)-(−)-2-nitro-1-(2-oxiranyl-methyl)-1H-imidazole, 0.24 g (5.4 mmole) of 1H-aziridine, and 3.5 mL of 99:1 absolute ethanol:triethylamine is heated at reflux for 10 minutes, cooled, and concentrated. The residue is crystallized from 99:1 absolute ethanol:triethylamine to give product, mp 119.5°–121° C. $[\alpha]D^{25}$=−28.7° [c1.15, chloroform].

(f) (R)-(+)-α-1-(2-nitro-1-imidazolyl)-3-(2-bromoethylamino)-2-propanol, monohydrobromide A mixture of 8.5 g (33.2 mmole) of (S)-3-[2-hydroxy-3-(2-nitro-1H-imidazol-1-yl)propyl]-2-oxazolidinone and 51 mL of 31% hydrogen bromide in acetic acid is stirred at room temperature for 7 days. The precipitated solids are collected by filtration, washed successively with 70 mL of 2:1 diethyl ether:2-propanol then 100 mL of diethyl ether, and air dried to leave 11.8 g of product, mp 149°–151° C. (decomposition). The product is dissolved in 100 mL of hot methanol, the solution filtered through Celite, and the filtrate stored at 25° C. for 6 hours then at 0°–5° C. for 8 hours. The solids are collected by filtration, washed with 30 mL of 1:1 diethyl ether:methanol, and dired at 55° C./150 mm/15 hours to give 7 g of pure product as the monohydrobromide salt, mp 154°–156° C. (decomposition), 100% optically pure by chiral HPLC; $[\alpha]D^{25}$ =+5.57° [c1, methanol].

Alternatively, to an ice-cold solution of 160 mL of 31% hydrogen bromide in acetic acid was added 31.2 g (95 mmole) of (S)-3-[3-(2-nitro-1H-imidazol-1-yl)-2-[(trimethylsilyl)oxy]propyl]-2-oxazolidinone, synthesized as described in (c), and the solution is allowed to slowly warm to 25° C. then stirred for 23.5 hours. The solids are collected by filtration, washed with 100 mL of 2:1 diethyl ether:2-propanol, and dried to leave 28.85 g of first crop material. The filtrate is poured slowly into a rapidly stirring solution of 1.2 L of 2:1 diethyl ether:2-propanol. The precipitated solids are collected by filtration, washed with ~200 mL of 2:1 diethyl ether:2-propanol, then dissolved in a mixture of 80 mL of 1:1 31% hydrogen bromide in acetic acid:2-propanol. The solution is stirred at 25° C. for 24 hours and the solids are collected by filtration then processed as above to leave 5.35 g of a second crop. The crops are combined and dissolved in 280 mL of hot methanol. The solution is maintained at 25° C. for 2 hours, then refrigerated for 4 hours. The solids are collected by filtration, washed with methanol, and dried to leave 17.62 g of product as the monohydrobromide salt, mp 157°–159° C. (decomposition), 100% optically pure by chiral HPLC; $\{\alpha]D^{25}$ =+5.55° [c1, methanol].

The filtrate is concentrated to a solid that is crystallized in ~60 mL of methanol as above to leave 3.8 g of second crop material, mp 152°–154° C. (decomposition). Further processing of the filtrate affords 1.5 g of third crop and 0.5 g of fourth crop materials, mp 145°–150° C. (decomposition). The second through fourth crops are combined and crystallized in 60 mL of hot methanol, with cooling at −20° C. for 7 hours, and further processing as above to give 4.59 g of product, 100% optically pure by chiral HPLC; $[\alpha]D^{25}$ =+5.71° [c1, methanol].

In another alternate procedure, treatment of (R)-(−)-α-(1-aziridinylmethyl)-2-nitro-1H-imidazole-1-ethanol, synthesized as described in (e), with aqueous hydrogen bromide in acetone, as described in *The Journal of Medicinal Chemistry*, 33, 2608 (1990), gives the product, mp 149°–150.5° C. (decomposition), 99.3% optically pure by chiral HPLC.

The NO Synthase Inhibitor

Any NO synthase inhibitor may be used in the invention to potentiate the activity of the imidazole or 1,2,4-triazole derivative. An NO synthase inhibitor suitable for use in the invention will generally give a positive result in one or more of the following three assays.

| ASSAY | REFERENCE | POSITIVE RESULT |
|---|---|---|
| Nitrite assay; stimulation of nitrite production from J774.2 macrophages with 1 μg/ml bacterial endotoxin (lipopolysaccharide, LPS) | Szabo et al (1993) Biochem. Biophys. Res. Commun. 196 825–830 | at least 50% inhibition of nitrite production at a concentration within the range of $10^{-8}$ to $10^{-3}$ M |
| Rabbit aorta strip cascade assay; inhibition of relaxation of rabbit aorta strips induced by NO release from 20 μM bradykinin stimulated porcine aortic endothelial cells | Moncada et al (1986) Proc. Natl. Acad. Sci. USA 83, 9164–9168 | at least 50% inhibition of of rabbit aorta strip relaxation at a concentration within the range of $10^{-8}$ to $10^{-5}$ M |
| Arterial Blood pressure assay; increase in mean arterial blood pressure (MABP) in anaesthetised rats | Thiemermann et al (1991) Br. J. Pharmacol 104, 31–38 | at least 10% increase in MABP at a concentration within the range of 1 to 50 mg/kg i.v. |

In the nitrite assay, nitrite production (an indicator of NO synthesis) may be measured in the supernatant of J774.2 macrophages as follows. The cells are cultured in 96-well plates with 200 μl culture medium until cells reach confluence (approximately 62000 cells/well). To induce NO synthase, fresh culture medium containing E. Coli LPS (1 μg ml$^{-1}$) is added. Nitrite accumulation in the cell culture medium is measured 24 hours after the application of LPS. To assess the effects of a possible NO synthase inhibitor on induction of nitrite production, the inhibitors are added 30 min prior to LPS to the cells. Nitrite is measured by adding 100 μl of Griess reagent (1% sulfanilamide and 0.1% naphthylethylenediamide in 5% phosphoric acid) to 100 μl samples of cell culture medium. The optical density at 550 nm ($OD_{550}$) is measured using a microplate reader (e.g. a Molecular Devices reader, Molecular Devices, Richmond, Calif., USA). Nitrite concentrations are calculated by comparison with $OD_{550}$ of standard solutions of sodium nitrite prepared in culture medium.

The rabbit aorta strip assay may be carried out as follows. Porcine aortic endothelial cells are cultured on microcarriers. A column containing 2–6×10$^7$ endothelial cells on microcarrier beads is perfused (5 ml/min) with Krebs' buffer gassed with 95% $O_2$/5% $CO_2$ at 37° C. The column effulent superfuses a cascade of up to four RbAs (sprirally cut strips of rabbit thoracic aorta denuded of endothelium). The delay between the endothellial cells in the column and consecutive RbAs is 1, 4, 7 and 10 sec, repsectively. The bioassay tissues are contracted with a continuous infusion over the tissues (o.t.) of either the 11α, 9α-epoxymethano analogue of prostaglandin $H_2$ (U-46619; 30–60 nM) or with phenylephrine hydrochloride (50 nM). The sensitivity of the RbAs is adjusted so that they are relaxed to a similar extent by a standard dose of glyceryl trinitrate (nitroglycerin, n$_3$Gro; 50 nM o.t.). A 1 min infusion of bradykinin (20 nM) through the column (t.c.) is used as the standard stimulus for EDRF release, although the calcium ionophore A23187 (0.2–5 μM t.c.) is used occasionally. The possible inhibitors studied are dissolved in 0.9% NaCl and infused either o.t. or t.c. with a peristaltic micropump. Their inhibitory potency is calculated from concentration-response curves. These are constructed by measuring the EDRF-induced relaxation of the uppermost RbA in the presence of the inhibitor and expressed as a percentage of the mean of two bracketing control responses.

The arterial blood pressure assay may be carried out as follows. Male Wistar rats (245–320 g; from e.g. Glaxo Laboratories Ltd., Greenford, Middlesex or Harland UK Ltd, Bicester, Oxon) are anaesthetized with thiopentone sodium (Trapanal; 120 mg kg$^{-1}$, i.p.). The trachea is cannulated to facilitate respiration and the rectal temperature is maintained at 37° C. by means of a rectal probe connected to a homeothermic blanket (e.g. from BioScience, Sheerness, Kent, U.K.). The right carotid artery is cannulated and connected to a pressure transducer (e.g. a Transamerica type 4-422-0001 pressure transducer) for the measurement of mean arterial blood pressure and heart rate on a polygraph recorder (e.g. a Glass model 7D recorder, Glass Instruments, Quincy, Mass., U.S.A.). The left jugular vein, the right femoral vein and the left femoral vein are cannulated for the administration of possible NO synthase inhibitors.

Examples of suitable NO synthase inhibitors are L-arginine derivatives, L-citrulline derivatives, ornithine derivatives, guanidine derivatives, indazole derivatives, hydroquinone derivatives and amidino derivatives. Specific examples of suitable NO synthase inhibitors include nitro-L-arginine (NOARG), nitro-L-arginine methyl ester (L-NAME), L-N-monomethyl-L-arginine (L-NMMA), L-N$^G$-nitro arginine p-nitroaniline (L-NAPNA), L-N$^G$-aminoarginine, 7-nitroindazole, phenidone, 3-amino-1-[m-trifluoro-methyl)phenyl]-2-pyrazoline (BW 755C), hydroquinone and dithiothreitol.

L-arginine and ornithine derivatives of the following formula (1) such as L-NMMA which may be useful in the invention are disclosed in GB-A-2 240 041 as useful in the treatment of toxic shock and other types of systemic hypotension:

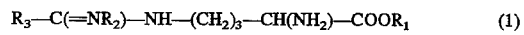

$$R_3—C(=NR_2)—NH—(CH_2)_3—CH(NH_2)—COOR_1 \quad (1)$$

wherein $R_1$ is hydrogen, methyl or ethyl; $R_2$ is hydrogen or $NO_2$; and $R_3$ is amino, methylamino, ethylamino, methyl or ethyl.

The therapeutic use of other L-arginine derivatives excluding L-NMMA which may be useful in the invention is disclosed in EP-A-0 446 699. These derivatives have the formulae (2a), (2b) and (2c):

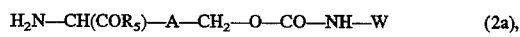

$$H_2N—CH(COR_5)—A—CH_2—O—CO—NH—W \quad (2a),$$

$$H_2N—CH(COR_5)—CH=CH—CH—NH—C(=Y)—NH—W (2b),$$

and

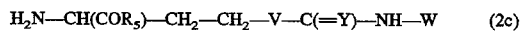

$$H_2N—CH(COR_5)—CH_2—CH_2—V—C(=Y)—NH—W \quad (2c)$$

wherein A is —(CH$_2$)$_2$—, —(CH$_2$)$_3$— or —CH=CH—; W is CN, cyclopropyl, 2-propyne, 2,3-butadiene or NHR$_6$ wherein R$_6$ is hydrogen, CF$_3$, CH$_2$CF$_3$ or C$_1$–C$_6$ alkyl; R$_5$ is an amino acid or OM wherein M is hydrogen, C$_1$–C$_6$ alkyl, benzyl, phenyl or pivoyl methyl ether, Y is O or NR$_7$ wherein R$_7$ is hydrogen, CF$_3$, —CH$_2$CF$_3$ or C$_1$–C$_6$ alkyl; and V is —CH$_2$—NH—, —(CH$_2$)$_2$—NH—, —NH—NH—, —CH$_2$—NH—NH—, —CH$_2$—O—NH— or —O—NH$_2$—; with the provisos that (i) when V is —NH—NH— or —(CH$_2$)$_2$—NH—, Y is O, (ii) when V is —CH$_2$—NH—, Y is NH$_2$ and W is NHR$_6$, R$_6$ is not hydrogen, and (iii) when Y is O and W is NHR$_6$, V is —CH$_2$—NH— or —(CH$_2$)$_2$—NH—.

WO 93/13055 discloses amidino derivatives of formula (3) which may be useful in the invention

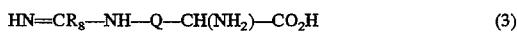

wherein $R_8$ is a $C_{1-6}$ straight or branched chain alkyl group, a $C_{2-6}$ alkenyl group, a $C_{2-6}$ alkynyl group, a $C_{3-6}$ cycloalkyl group or a $C_{3-6}$ cycloalkyl—$C_{1-6}$ alkyl group;

Q is an alkylene, alkenylene or alkynylene group having 3 to 6 carbon atoms and which may optionally be substituted by one or more $C_{1-3}$ alkyl groups;

a group of formula —$(CH_2)_pE(CH_2)_q$— where p is 2 or 3, q is 1 or 2 and E is $S(O)_f$ where f is 0, 1 or 2, or $NR_9$ where $R_9$ is H or $C_{1-6}$ alkyl; or a group of formula —$(CH_2)_rG(CH_2)_s$— where r is 0, 1 or 2, s is 0, 1 or 2 and G is a 3 to 6 membered carbocyclic or heterocyclic ring which may be optionally substituted by one or more suitable substituents such as $C_{1-6}$ alkyl, $C_{1-6}$ alkoxy, hydroxy, halo, nitro, cyano, trifluoro $C_{1-6}$ alkyl, amino, $C_{1-6}$ alkylamino or di$C_{1-6}$ alkylamino; and salts, and pharmaceutically acceptable esters and amides thereof.

7-Nitro indazole and derivatives thereof which may be useful in the invention are described in Moore et al (1993) Br. J. Pharmacol. 110, 219–224 as NO synthase inhibitors with therapeutic effects. L-NAPNA is described in Babbedge et al (1992) Br. J. Pharmacol. 107, 194P as an NO synthase inhibitor, and may be useful in the invention. See Moncada et al (1986) Proc. Natl. Acad. Sci. USA 83, 9164–9168 for a description of the activities of phenidone, 3-amino-1-[m-(trifluoromethyl)phenyl]-2-pyrazoline (BW 755C), hydroquinone and dithiothreitol.

The Administration of the Imidazole or 1,2,4-Triazole Derivative and NO Synthase Inhibitor to a Subject The method of the invention can be applied to improving the condition of a subject having any of a variety of types of solid tumour. The method is particularly useful for the treatment of hypoxic tumours and tumours which are susceptible to being made hypoxic. The method may also be particularly useful for treatment of tumours rich in enzymes which activate bioreductive compounds. Such enzymes include cytochrome P450, NADPH-dependent cytochrome P450 reductase, DT-diaphorase and xanthine oxidase. Examples of tumours which may be treated include melanomas, glioblastomas, and tumours of the lung, breast, cervix, ovary, prostate, head, neck, colon, rectum, stomach, bladder and oesophagus.

The method of the invention may be combined with radiation treatment. However, the presence of the NO synthase inhibitor will reduce the effectiveness of radiation treatment by causing hypoxia in the tumour. The compounds should therefore be administered post-radiation and, in the case of clinical regimens involving multiple doses of radiation, the effects of the compounds should be allowed to wear off before the next dose of radiation. Thus, radiation should generally be given at least 12 hours, for example from 12 hours to 7 days or 24 hours to 7 days after the compound administered last.

The imidazole or 1,2,4-triazole derivative and the NO synthase inhibitor are preferably administered simultaneously or close to each other in time. In particular, the two compounds are preferably administered less than twelve hours apart, more preferably less than two hours apart, most preferably less than one hour apart. The two compounds may be administered in any order; i.e. the imidazole or 1,2,4-triazole derivative may be administered before the NO synthase inhibitor, or the NO synthase inhibitor may be administered before the imidazole or 1,2,4-triazole derivative. However, the imidazole or 1,2,4-triazole derivative is preferably administered a short time (e.g. less than one hour) before the NO synthase inhibitor.

The NO synthase inhibitor and imidazole or 1,2,4-triazole derivative can be administered in a variety of dosage forms: e.g. orally, in the form of tablets, capsules, sugar or film coated tablets, liquid solutions or suspensions; rectally, in the form of suppositories; or parenterally, e.g. intramuscularly, or by intravenous injection or infusion.

The NO synthase inhibitor and imidazole or 1,2,4-triazole derivative are administered in amounts sufficient for a synergistic therapeutic effect. Such amounts will improve the condition of the subject. The NO synthase inhibitor will generally be administered in an amount sufficient to increase the level of hypoxia of the tumour; such an amount should generally potentiate the therapeutic effect of the imidazole or 1,2,4-triazole derivative. Systemic effects of the NO synthase inhibitor may limit the dosage. These effects are due to the vasoconstrictive properties of NO synthase inhibitors, seen as increased blood pressure and/or peripheral vascular resistance. The imidazole or 1,2,4-triazole derivative will generally be administered in an amount sufficient to kill tumour cells when administered together with the NO synthase inhibitor.

The exact dose of the NO synthase inhibitor and the imidazole or 1,2,4-triazole derivative will depend on a variety of factors such as the type of cancer, the condition of the subject and the weight of the subject. However, a suitable dose of the NO synthase inhibitor may be from 0.1 µg/kg to 1 g/kg of the subject's body weight, for example from 0.05 to 20 mg/kg. A suitable dose of the imidazole or 1,2,4-triazole derivative may be from 1 µg/kg to 1 g/kg, for example from 100 to 300 mg/kg.

Each of the two compounds is suitably administered in the form of a pharmaceutical composition comprising the compound as active ingredient and a pharmaceutically acceptable carrier or diluent. The two compounds may be administered in the same pharmaceutical composition, but it will usually be more convenient to administer them in separate compositions. The two compounds may be provided as a kit comprising two pharmaceutical compositions, each pharmaceutical composition comprising one of the compounds.

The pharmaceutical compositions containing the imidazole or 1,2,4-triazole derivative and the NO synthase inhibitor may be prepared following conventional methods.

For example, solid oral forms may contain, together with the active compounds, diluents, e.g., lactose, dextrose, saccharose, cellulose, corn starch or potato starch; lubricants, e.g. silica, talc, stearic acid, magnesium or calcium stearate, and/or polyethylene glycols; binding agents e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances conventionally used in pharmaceutical formulations. Said pharmaceutical preparations may be manufactured in a known manner, for example, by means of mixing, granulating, tabletting, sugar-coating, or film coating processes.

The liquid dispersions for oral administration may be e.g. syrups, emulsions and suspensions. The syrups may contain as carriers, for example, saccharose or saccharose with glycerine and/or mannitol and/or sorbtol.

The suspensions and the emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solutions for intravenous injection or infusion may contain as carrier, for example, sterile water or preferably they may be in the form of sterile, aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin.

The following Examples illustrate the invention.

EXAMPLES

METHODS USED IN EXAMPLES 1-3 AND COMPARATIVE EXAMPLES 1 AND 2

1. Tumours: Transplantable murine sarcomas, RIF-1 and KHT, and carcinoma SCCVII/Ha in male or female $C_3H$/He mice were used for experiment. These tumours were routinely implanted intradermally on the mouse back, 2 cm from the base of the tail, from $2\times10^5$ tumour cells in 0.05 ml of culture medium.

Tumours were used for experiment at a mean diameter of 5-6 mm, (100-200 $mm^3$ volume), 10-14 days after implant. Anaesthesia was not used for experiment, but mice were gently restrained in specially designed jigs, to expose the tumour on the mouse back.

2. Nitroarginine (nitro-L-arginine, NOARG) was given by bolus intravenous injection in phosphate buffered saline at doses of 0.005-20 mg/kg, 0.005 ml/g body weight.

RB6145 (1-(2-nitro-1-imidazolyl)-3-(2-bromoethylamino)-2-propanol) was given by intraperitoneal injection in acetate buffer pH 5.3, at 100-300 mg/kg, 0.02 ml/g body weight.

Tirapazamine (SR4233, 3-amino-1,2,4-benzotriazine-1,4-dioxide) was given by intraperitoneal injection in phosphate buffered saline at 50 mg/kg, 0.02 ml/g body weight.

Cyclophosphamide was injected intraperitoneally at 100 mg/kg, in phosphate buffered saline, 0.02 ml/g mouse body wt.

Nitro-arginine methyl ester (L-NAME) was injected intravenously at 10 mg/kg, in phosphate buffered saline, 0.005 ml/g mouse body weight. In addition, mice were given L-NAME in the drinking water at 1 mg/ml, immediately after the bolus injection, and continued for the duration of the experiment.

$^{31}$P Magnetic Resonance Spectroscopy (MRS) In vivo $^{31}$P MRS experiments were carried out using a 4.7 Tesla, 30 cm horizontal bore magnet, with a SISCO 200 spectrometer. A 7 mm diameter surface coil was placed over the tumour for Rf pulsing and signal collection. Acquisition parameters were set to minimise contamination of the signal from underlying muscle. Each spectrum comprised 256 scans with a 2 sec delay, giving a total acquisition time of 8 min.

MRS experiments were carried out as follows: The mouse was catheterised via the tail vein for injection of nitroarginine. RB6145 was given by i.p. injection. The mouse was placed in the restraining jig and left for 15-20 min for the mouse to settle down. The mouse and jig were placed in the magnet, the surface coil placed over the tumour and with the catheter attached to a syringe outside the body of the magnet. A control $^{31}$P MR spectrum was collected. The required amount of nitroarginine was injected and a series of spectra collected at intervals for up to 2 hr after administration, without moving the mouse from its position in the magnet. This approach allows each mouse to be used at its own control. For later time points (6 hr and 24 hr), the mouse was removed from the jig, returned to its cage and replaced in the jig at the required time.

For experiments involving RB6145 and nitroarginine, a control spectrum was collected, the mouse removed from the jig and RB6145 injected i.p. The mouse was returned to the jig and replaced in the magnet, for collection of a further spectrum prior to injection of nitroarginine, after which the above procedure was followed.

Spectra were analysed using an in-house baseline and Lorentzian curve fitting programme, which calculated the area under each component peak of the spectrum. Effects on tumour metabolism were observed as changes in low energy, inorganic phosphate relative to high energy phosphates, ATP and phosphocreatine. Data were expressed as the ratio of the inorganic phosphate peak area to the sum of all peak areas, or Pi/total. Tumour pH was also estimated from the chemical shift of the Pi peak relative to the alpha or gamma ATP peaks.

4. Survival Experiments: RB6145 or tirapazamine was given i.p. followed by i.v. nitroarginine 15 min later. Tumours were excised 18-24 hr after treatment, minced with scissors and digested to a single cell suspension for 30 min at 37° C., using an enzyme cocktail of pronase 6 mg, DNAse 2 mg, collagenase 2 mg per 10 ml phosphate buffered saline, for SCCVII/Ha and RIF-1 tumours, and in 0.4 ml 5% trypsin 1:250 and DNAse 2.5 mg per 10 ml phosphate buffered saline for KHT. Cell suspensions were centrifuged, washed and counted using a haemocytometer, then diluted prior to plating. SCCVII/Ha and RIF-1 cells were plated into liquid medium, RPMI 1640 with 15% foetal calf serum, glutamine and antibiotics. KHT cells were plated into soft agar medium, Ham's F10 with 10% newborn calf serum containing irradiated cells and rat red blood cells as a feeder layer. Plates were incubated for 12-14 days, after which time SCVII/Ha and RIF-1 colonies were fixed and stained with methylene blue. Colonies were scored by eye (or under low power magnification for KHT).

Surviving fraction was calculated after correction for plating efficiency of untreated controls. Relative surviving fraction was calculated as above but included a correction for reduction in tumour cell yield during the digestion of the tumour to a single cell suspension.

5. Growth Delay Assay: The effect of drug treatment on growth of KHT tumours implanted as described above was assessed by measuring the time taken to reach 4× the initial treatment volume. Tumour volume was determined from three orthogonal diameters according to the equation:

volume=π/6($d1 \times d2 \times d3$)

EXAMPLE 1: $^{31}$P MRS Experiments

These experiments were carried out to determine the effect of RB6145 and nitroarginine on tumour oxygenation.

Figure 2:
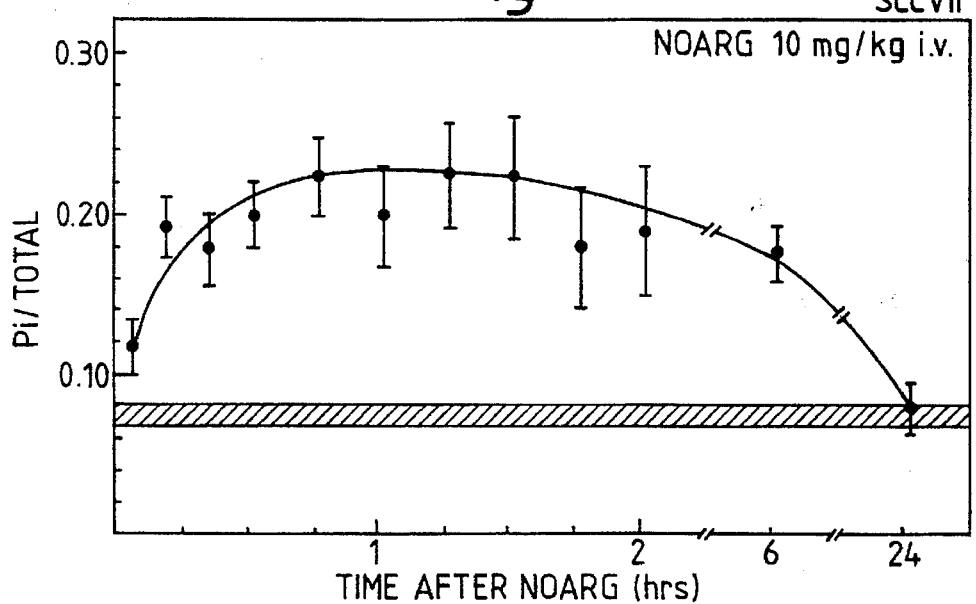
FIG. 2: This figure gives Pi/total with time after 10 mg/kg intravenous (i.v.) nitroarginine in the SCCVII/Ha tumour. Pi/total is increased 2–3 fold over control for up to 6 hr after injection, returning to control levels by 24 hr. Shaded area gives Pi/total for control tumours prior to treatment. Points are means±standard error (s.e.) for 7 mice. Data points are plotted at the mid-point of the 8 min spectrum collection time.

An increase in Pi/total is indicative of tumour hypoxia and a decrease is indicative of increasing oxygenation. FIG. 2 shows the results after 10 mg/kg i.v. nitroarginine in the SCCVII/Ha tumour. Pi/total is increased 2-3 fold over control for up to 6 hr after injection, returning to control levels by 24 hr. The shaded area gives Pi/total for control tumours prior to treatment.

Similar increases in Pi/total were observed for the KHT and RIF-1 tumours after injection of 10 mg/kg i.v. nitroarginine, i.e. the increase in Pi/total was maintained for at least 6 hrs with a return to control levels by 24 hrs.

| Time after Nitroarginine | Pi/total | |
|---|---|---|
| | Nitroarginine Alone | RB6145 + Nitroarginine |
| Control | 0.094 ± 0.012 | 0.100 ± 0.010 |
| 30 min | 0.163 ± 0.023 | 0.173 ± 0.010 |
| 60 min | 0.190 ± 0.014 | 0.195 ± 0.014 |
| 120 min | 0.200 ± 0.027 | 0.218 ± 0.020 |
| 24 hr | 0.130 ± 0.0053 | 0.450 ± 0.100 |

The increase in Pi/total to 0.45 at 24 hr after RB6145 plus nitroarginine is indicative of severe tumour hypoxia, and contrasts that observed for nitroarginine alone in the SCCVII/Ha tumour at this time, where Pi/total was back to control values. RB6145 alone has no significant effect on Pi/total.

EXAMPLE 2: Survival Experiments

Nitroarginine in Combination with RB6145

Figure 3A:
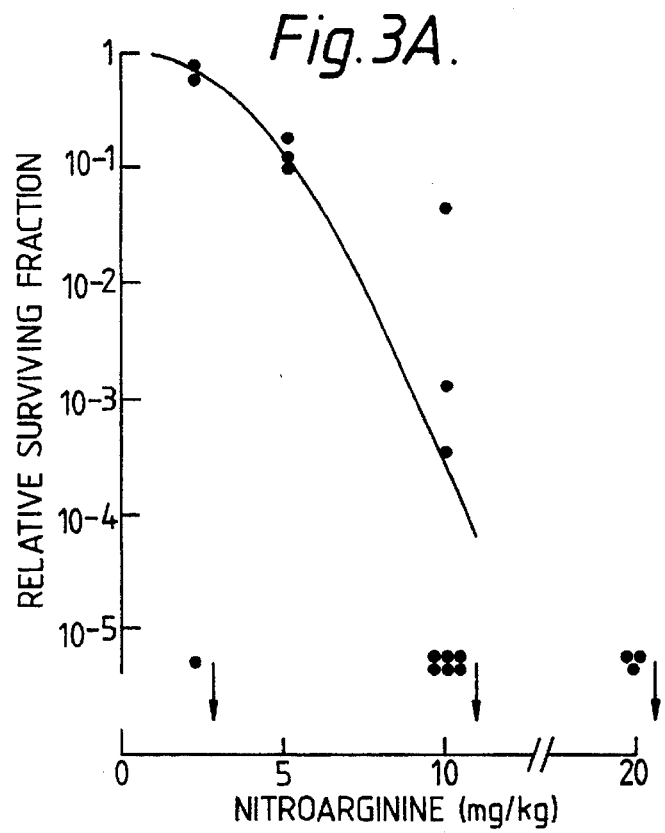
FIGS. 3A and 3B: These figures give the relative cell survival of the KHT tumour after treatment with RB6145 followed 15 min later by nitroarginine, using the in vivo/in vitro clonogenic assay 18–24 hr after treatment A: Nitroarginine dose response with 300 mg/kg intraperitoneal (i.p.) RB6145, and B: RB6145 dose response with 10 mg/kg i.v. nitroarginine. Points are geometric means±s.e. Downward arrows indicate cell survival was undetectable below these levels.
Figure 3B:
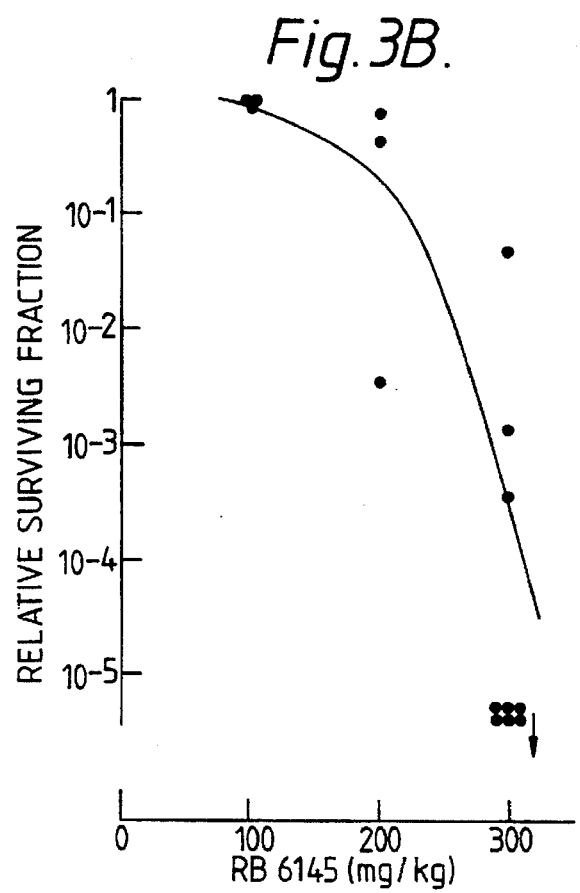

FIG. 3 gives the relative cell survival of the KHT tumour after treatment with RB6145 followed 15 min later by nitroarginine. A: Nitroarginine dose response with 300 mg/kg i.p. RB6145, and B: RB6145 dose response with 10 mg/kg i.v. nitroarginine.

Neither nitroarginine alone at 10 mg/kg i.v., nor RB6145 alone at 300 mg/kg i.p. significantly affected tumour cell survival.

COMPARATIVE EXAMPLE 1: Survival Experiment

Nitroarginine in Combination with Tirapazamine (SR4233, 3-Amino-1,2,4-Benzotriazine-1,4-Dioxide)

Nitroarginine at 10 mg/kg i.v. given 15 min after 50 mg/kg i.p. tirapazamine had no effect on SCCVII tumour cell survival, using an in vivo/in vitro clonogenic assay 18–24 hr after treatment. The results are shown in the following Table.

| | Relative Surviving Fraction |
|---|---|
| NOARG | 1.52 |
| Tirapazamine | 0.84 |
| Tirapazamine + NOARG | 0.71, 1.90, 0.93 |

COMPARATIVE EXAMPLE 2: Tumour Growth Delay

Nitro-Arginine Methyl Ester (L-NAME) in Combination With Cyclophosphamide

The following Table shows the time taken by KHT tumours to reach 4 times their initial volume.

| | Time to 4x initial volume (days) |
|---|---|
| Control | 3.8 |
| Cyclophosphamide | 13.95 ± 1.10 |
| Cyclophosphamide followed one hour later by L-NAME | 15.11 ± 0.90 |

Clearly, the NOS inhibitor L-NAME given after cyclophosphamide does not enhance the growth delay induced by this agent in the KHT tumour.

EXAMPLE 3: Survival Experiment

Timing of RB6145 and NOARG Administration

Figure 4:
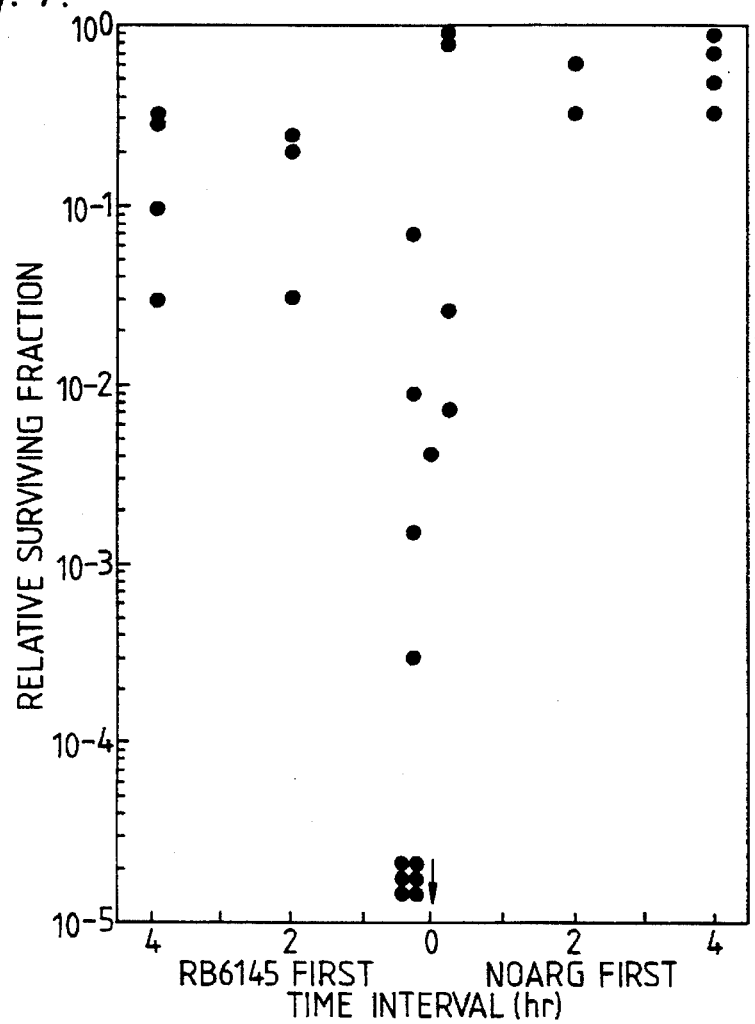
FIG. 4: This figure gives the relative cell survival of tumours 24 hr after treatment with RB6145 plus NOARG administered at various time intervals apart from each other.

FIG. 4 gives the relative cell survival of tumours after treatment with RB6145 (300 mg/kg i.p.) and NOARG (10 mg/kg i.v.) administered at various time intervals apart from each other. Tumours were excised and plated for survival 24 hrs after treatment. Greatest killing was attained by giving RB6145 a short time before NOARG.

We claim:

1. A method of treating a human or animal subject having a solid tumor selected from the group consisting of melanomas, glioblastomas and tumors of the lung, breast, cervix, ovary, prostate, head, neck, colon, rectum, stomach, bladder and oesophagus, which method comprises the step of administering to the subject a synergistic therapeutically effective amounts of;

a nitric oxide (NO) synthase inhibitor which gives a positive result in at least one assay selected from the group consisting of the Nitrite assay, the Rabbit aorta strip cascade assay and the Arterial Blood pressure assay, said nitric oxide synthase inhibitor being selected from the group consisting of nitro-L-arginine (NOARG), nitro-L-arginine methyl ester (L-NAME), L-N-monomethyl-arginine (L-NMMA), L-N$^G$-nitroarginine p-nitroaniline (L-NAPNA), L-N$^G$-aminoarginine, 7-nitroindazole, phenidone, 3-amino-1-[m-(trifluoromethyl)phenyl]-2-pyrazoline, hydroquinone, and dithiothreitol, and an imidazole derivative of formula (A)

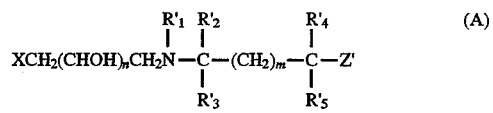

wherein X is

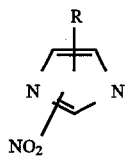

in which R is H or $C_1-C_6$ alkyl;

each of $R'_1$ to $R'_5$ is H or $C_1-C_6$ alkyl;

m is 0 or 1;

n is 1; and

Z' is halogen or —OCOR$_6$ wherein R$_6$ is $C_1-C_6$ alkyl or halo($C_1-C_6$)alkyl;

or a physiologically acceptable acid addition salt thereof.

2. A method according to claim 1 wherein X is an imidazol-1-yl group having a nitro group in the 2-position.

3. A method according to claim 1 wherein m is 0.

4. A method according to claim 1 wherein n is 1.

5. A method according to claim 1 wherein $R'_1$ is hydrogen and each of $R'_2$ to $R'_5$ is independently hydrogen or methyl.

6. A method according to claim 5 wherein each of $R'_1$ to $R'_5$ is hydrogen.

7. A method according to claim 2 wherein Z' is selected from the group consisting of halogen, $C_2$–$C_6$ alkanoyloxy, and per- and poly-fluoro-$C_2$–$C_6$ alkanoyloxy.

8. A method according to claim 7 wherein Z' is bromine.

9. A method according to claim 1 wherein the physiologically acceptable acid addition salt of the imidazole derivative is a salt with an acid selected from the group consisting of hydrochloric, hydrobromic and hydroiodic acid.

10. A method according to claim 1 wherein the said derivative of formula (A) or salt thereof is selected from the group consisting of 1-(2-nitro-1-imidazolyl)-3-(2-chloroethylamino)-2-propanol, 1-(2-nitro-1-imidazolyl)-3-(2-bromoethylamino)-2-propanol, 1-(2-nitro-1-imidazolyl)-3-(2-iodoethylamino)-2-propanol, 1-(2-nitro-1-imidazolyl)-3-(2-fluoroethylamino)-2-propanol, 1-(2-nitro-1-imidazolyl)-3-(2-acetoxyethylamino)-2-propanol, 1-(2-nitro-1-imidazolyl)-3-(2-trifluoroacetoxyethylamino)-2-propanol, 1-(2-methyl-4-nitro-1-imidazolyl)-3-(2-chloroethylamino)-2-propanol, 1-(2-methyl-4-nitro-1-imidazolyl)-3-(2-bromoethylamino)-2-propanol, 1-(2-methyl-4-nitro-1-imidazolyl)-3-(2-iodoethylamino-2-propanol, 1-(2-methyl-5-nitro-1-imidazolyl)-3-(2-chloroethylamino)-2-propanol, 1-(2-methyl-5-nitro-1-imidazolyl)-3-(2-bromoethylamino)-2-propanol, 1-(2-methyl-5-nitro-1-imidazolyl)-3-(2-iodoethylamino)-2-propanol, 1-(2-methyl-5-nitro-1-imidazolyl)-3-(2-fluoroethylamino)-2-propanol, 1-(2-nitro-1-imidazolyl)-3-(3-bromopropylamino)-2-propanol, 1-(2-nitro-1-imidazolyl)-3-(1-chloro-2-methyl-2-propylamino)-2-propanol, 1-(2-nitro-1-imidazolyl)-3-(1-bromo-2-methyl-2-propylamino)-2-propanol, 1-(2-nitro-1-imidazolyl)-3-(dl-threo-2-chloro-3-butylamino)-2-propanol, 1-(2-nitro-1-imidazolyl)-3-(dl-threo-2-bromo-3-butylamino)-2-propanol, 1-(2-nitro-1-imidazolyl)-3-(2-chloro-2,3-dimethyl-3-butylamino)-2-propanol, 1-(2-nitro-1-imidazolyl)-3-(2-bromo-2,3-dimethyl-3-butylamino)-2-propanol, and physiologically acceptable acid addition salts thereof.

11. A method according to claim 1 wherein the said derivative of formula (A) or salt thereof is selected from the group consisting of 1-(2-nitro-1-imidazolyl)-3-(2-chloroethylamino)-2-propanol hydrochloride, 1-(2-nitro-1-imidazolyl)-3-(2-bromoethylamino)-2-propanol hydrobromide, 1-(2-nitro-1-imidazolyl)-3-(2-iodoethylamino)-2-propanol hydriodide, 1-(2-nitro-1-imidazolyl)-3-(2-fluoroethylamino)-2-propanol hydrochloride, 1-(2-nitro-1-imidazolyl)-3-(2-acetoxyethylamino)-2-propanol, 1-(2-nitro-1-imidazolyl)-3-(2-trifluoroacetoxyethylamino)-2-propanol, 1-(2-methyl-4-nitro-1-imidazolyl)-3-(2-chloroethylamino)-2-propanol hydrochloride, 1-(2-methyl-4-nitro-1-imidazolyl)-3-(2-bromoethylamino)-2-propanol hydrobromide, 1-(2-methyl-4-nitro-1-imidazolyl)-3-(2-iodoethylamino-2-propanol hydriodide, 1-(2-methyl-5-nitro-1-imidazolyl)-3-(2-chloroethylamino)-2-propanol hydrochloride, 1-(2-methyl-5-nitro-1-imidazolyl)-3-(2-bromoethylamino)-2-propanol hydrobromide, 1-(2-methyl-5-nitro-1-imidazolyl)-3-(2-iodoethylamino)-2-propanol hydriodide, 1-(2-methyl-5-nitro-1-imidazolyl)-3-(2-fluoroethylamino)-2-propanol hydrochloride, 1-(2-nitro-1-imidazolyl)-3-(3-bromopropylamino)-2-propanol hydrobromide, 1-(2-nitro-1-imidazolyl)-3-(1-chloro-2-methyl-2-propylamino)-2-propanol hydrochloride, 1-(2-nitro-1-imidazolyl)-3-(1-bromo-2-methyl-2-propylamino)-2-propanol hydrobromide, 1-(2-nitro-1-imidazolyl)-3-(dl-threo-2-chloro-3-butylamino)-2-propanol hydrochloride, 1-(2-nitro-1-imidazolyl)-3-(dl-threo-2-bromo-3-butylamino)-2-propanol hydrobromide, 1-(2-nitro-1-imidazolyl)-3-(2-chloro-2,3-dimethyl-3-butylamino)-2-propanol hydrochloride, and 1-(2-nitro-1-imidazolyl)-3-(2-bromo-2,3-dimethyl-3-butylamino)-2-propanol hydrobromide.

12. A method according to claim 1 wherein the derivative of formula (A) or salt thereof and the NO synthase inhibitor are administered simultaneously or less than one hour apart.

13. A method according to claim 1 wherein the subject is also treated with radiation.

14. A method according to claim 1, wherein the said derivative of formula (A) is an imidazole derivative of the formula (B):

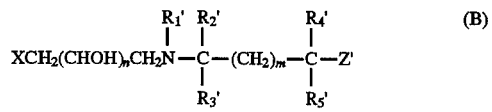

wherein X, $R'_1$ to $R'_5$, m, n, and Z' are as defined in claim 24 with the proviso that m is 1 when X represents

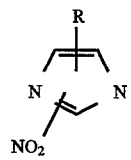

and R is hydrogen or a $C_1$–$C_6$ alkyl group, $R'_1$ is hydrogen, each of $R'_2$ to $R'_5$ is independently selected from the group consisting of hydrogen and $C_1$–$C_6$ alkyl, and Z' represents halogen.

15. A method according to claim 1 wherein the said derivative of formula (A) is an imidazole derivative of formula (C)

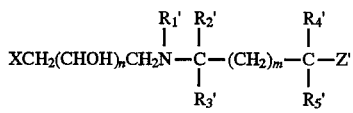

wherein m is 0, n is 1, X represents

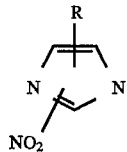

R is hydrogen or a $C_1$–$C_6$ alkyl group, $R'_1$ is hydrogen, each of $R'_2$ to $R'_5$ is independently selected from the group consisting of hydrogen and $C_1$–$C_6$ alkyl, and Z' represents halogen.

16. A pharmaceutical composition comprising a pharmaceutically acceptable carrier or diluent and, in amounts sufficient for a synergistic therapeutic effect, a NO synthase inhibitor selected from the group consisting of nitro-L-arginine (NOARG), nitro-L-arginine methyl ester (L-NAME), L-N-monomethyl-arginine (L-NMMA), L-N$^G$-nitroarginine p-nitroaniline (L-NAPNA), L-N$^G$-aminoarginine, 7-nitroindazole, phenidone, 3-amino-1-[m-(trifluoromethyl)phenyl]- 2-pyrazoline, hydroquinone, and dithiothreitol, and an imidazole derivative of formula (A)

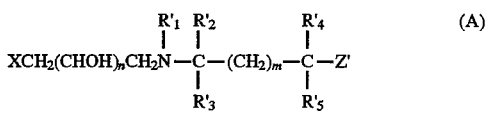

wherein X is

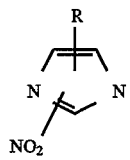

in which R is hydrogen or $C_1$–$C_6$ alkyl;

each of $R'_1$ to $R'_5$ is hydrogen or $C_1$–$C_6$ alkyl;

m is 0 or 1;

n is 1; and

Z' is halogen or —OCOR$_6$ wherein R$_6$ is $C_1$–$C_6$ alkyl or halo ($C_1$–$C_6$) alkyl;

or a physiologically acceptable acid addition salt thereof.

17. A method according to claim 1, wherein the NO synthase inhibitor is nitro-L-arginine and the derivative of formula (A) or a salt thereof is 1-(2-nitro-1-imidazolyl)-3-(2-bromoethylamino)-2-propanol hydrobromide.

* * * * *